United States Patent
Randlov et al.

(10) Patent No.: US 10,524,669 B2
(45) Date of Patent: Jan. 7, 2020

(54) APPARATUS AND METHOD FOR DETERMINING A PHYSIOLOGICAL CONDITION

(71) Applicant: Novo Nordisk A/S, Bagsvaerd (DK)

(72) Inventors: Jette Randlov, Vaerlose (DK); Jon Ulrich Hansen, Herlev (DK); Jens Ulrik Poulsen, Virum (DK)

(73) Assignee: Novo Nordisk A/S, Bagsvaerd (DK)

(*) Notice: Subject to any disclaimer, the term of this patent is extended or adjusted under 35 U.S.C. 154(b) by 457 days.

(21) Appl. No.: 14/055,508

(22) Filed: Oct. 16, 2013

(65) Prior Publication Data

US 2014/0058218 A1 Feb. 27, 2014

Related U.S. Application Data (60) Division of application No. 11/401,993, filed on Apr. 11, 2006, now abandoned, which is a continuation of
(Continued)

(30) Foreign Application Priority Data

Oct. 13, 2003 (DK) ................................ 2003 01510

(51) Int. Cl.
*A61B 5/0205* (2006.01)
*A61B 5/145* (2006.01)

(52) U.S. Cl.
CPC ........ *A61B 5/0205* (2013.01); *A61B 5/14532* (2013.01)

(58) Field of Classification Search
CPC .. G06F 19/34; G06F 19/3406; G06F 19/3431; G06F 19/345; A61B 5/14532; A61B 5/7275; A61B 5/7264
See application file for complete search history.

(56) References Cited

U.S. PATENT DOCUMENTS

| 4,509,531 A | 4/1985 | Ward |
| 5,844,862 A | 12/1998 | Cocatre-Zilgien |

(Continued)

FOREIGN PATENT DOCUMENTS

| JP | 7236643 | 9/1995 |
| WO | 01/13786 A1 | 3/2001 |

(Continued)

OTHER PUBLICATIONS

Watkins, Christopher JCH, and Peter Dayan. "Q-learning." Machine learning 8.3-4 (1992): 279-292. (Year: 1992).*
(Continued)

*Primary Examiner* — Niketa I Patel
*Assistant Examiner* — Nathan A Baldwin
(74) *Attorney, Agent, or Firm* — Wesley Nicolas (57) ABSTRACT

An apparatus for detecting a physiological condition in a person, comprising input structure for receiving at least two physiological parameters, processing structure for determining, from the received physiological parameters, a result signal indicative of the presence or onset of said physiological condition, and output structure for generating an output indicative of the result signal. The apparatus further comprises storage structure for storing a look-up table comprising a plurality of entries, each entry corresponding to a pre-calculated probability of the presence or onset of said physiological condition, the pre-calculated probabilities being determined by way of a mathematical process from previously monitored physiological parameters; and the processing means is adapted to process the received at least two physiological parameters to identify one of the plurality of entries of the look-up table, and to determine said result signal from the identified entry of the look-up table.

19 Claims, 4 Drawing Sheets

Related U.S. Application Data application No. PCT/DK2004/000697, filed on Oct. 12, 2004.

(60) Provisional application No. 60/513,617, filed on Oct. 23, 2003.

(56) References Cited

U.S. PATENT DOCUMENTS

| | | | |
|---|---|---|---|
| 5,997,476 A | 12/1999 | Brown | |
| 6,064,898 A * | 5/2000 | Aldrich | A61B 5/14532 600/316 |
| 6,151,517 A | 11/2000 | Honigs et al. | |
| 6,572,542 B1 * | 6/2003 | Houben | A61B 5/0472 128/920 |
| 2002/0106709 A1 * | 8/2002 | Potts | A61B 5/14532 435/14 |
| 2003/0199740 A1 | 10/2003 | Iliff | |
| 2004/0167418 A1 * | 8/2004 | Nguyen | A61B 5/00 600/513 |

FOREIGN PATENT DOCUMENTS

| | | |
|---|---|---|
| WO | 01/72208 A2 | 10/2001 |
| WO | 01/91854 A1 | 12/2001 |
| WO | 0215777 A1 | 2/2002 |
| WO | 02053024 A2 | 7/2002 |
| WO | 02/069798 A1 | 9/2002 |

OTHER PUBLICATIONS

JC Pickup: "Preliminary evaluation of a skin conductance meter for detecting hypoglycemia in diabetic patients." Diabetes Care. American Diabetes Association. vol. 5(3): 326-329 1982.

DJ Cox: "Perceived symptoms in the recognition of hypoglycemia." Diabetes Care, American Diabetes Association vol. 16(2): 519-527 1993.

Ka Hansen: "Teledyne Sleep Sentry: Evaluation in pediatric patients for detection of nocturnal hypoglycemia" Diabetes Care, American Diabetes Association vol. 6(6): 597-600 1983.

An Exisiting product awaiting FDA approval—see www.sleepsentry. com <http://www.sleepsentry.com>. (http://www.giantbiosensor. com/Low-Blood-Sugar-Alarm.html accessed Apr. 28 <http://www. giantbiosensor.com/Low-Blood-Sugar-Alarm.html%20accessed% 20April%2028>, 2014).

Malpas, SS, "Heart rate variability during hypoglycaemia," Diabetic Medicine, 1989, vol. 6, pp. 822-823.

* cited by examiner

| S1 | ΔS1 | S2 | ΔS2 | P |
|---|---|---|---|---|
| 1 | 1 | 1 | 1 | $P_{1111}$ |
| 1 | 1 | 1 | 2 | $P_{1112}$ |
| 1 | 1 | 2 | 1 | $P_{1121}$ |
| 1 | 1 | 2 | 2 | $P_{1122}$ |
| 1 | 1 | 3 | 1 | $P_{1131}$ |
| 1 | 1 | 3 | 2 | $P_{1132}$ |
| 1 | 2 | 1 | 1 | $P_{1211}$ |
| 1 | 2 | 1 | 2 | $P_{1212}$ |
| 1 | 2 | 2 | 1 | $P_{1221}$ |
| 1 | 2 | 2 | 2 | $P_{1222}$ |
| 1 | 2 | 3 | 1 | $P_{1231}$ |
| 1 | 2 | 3 | 2 | $P_{1232}$ |
| ... | ... | ... | ... | ... |
| 4 | 4 | 1 | 1 | $P_{4411}$ |
| 4 | 4 | 1 | 2 | $P_{4412}$ |
| 4 | 4 | 2 | 1 | $P_{4421}$ |
| 4 | 4 | 2 | 2 | $P_{4422}$ |
| 4 | 4 | 3 | 1 | $P_{4431}$ |
| 4 | 4 | 3 | 2 | $P_{4432}$ |

APPARATUS AND METHOD FOR DETERMINING A PHYSIOLOGICAL CONDITION

CROSS-REFERENCE TO RELATED APPLICATIONS

This application is a Divisional of U.S. Ser. No. 11/401,993, filed Apr. 11, 2006, which is a Continuation of International Application PCT/DK2004/000697 (published as WO 2005/037092), filed Oct. 12, 2004, which claimed priority of Danish Patent Application PA 2003 01510, filed Oct. 13, 2003, this application further claims priority under 35 U.S.C. § 119 of U.S. Provisional Application 60/513,617, filed Oct. 23, 2003, the contents of which are incorporated herein by reference.

FIELD OF THE INVENTION

This invention relates to the detection of a physiological condition, such as hypoglycaemia, in a patient. More particularly, the invention relates to an apparatus for detecting a physiological condition in a person, and to a method of alerting a patient to the risk of the presence of a physiological condition.

BACKGROUND OF THE INVENTION

One of the most frequent complications experienced by patients suffering from insulin dependant diabetes mellitus is the phenomenon of hypoglycaemia.

Hypoglycaemia is a physiological condition where the blood glucose level of the patient decreases below a certain value. Blood glucose levels below approx. 2.5 mmol/L may give rise to serious symptoms and may potentially even become dangerous for a diabetic patient, in particular, if the patient does not become aware of the condition, e.g. because the patient is sleeping or preoccupied with another activity, e.g. driving a car.

Already during the onset of hypoglycaemia more moderate drops of the blood glucose level, e.g. below approximately 3.8 mmol/L glucagon, cause epinephrine, growth hormone, and cortisol to be released, resulting in symptoms such as rise in pulse, lowering of the variability of the heart rate and increased perspiration.

Hence, there is a strong desire to allow for a monitoring of a patient to avoid an undetected occurrence of hypoglycaemia. Even though glucose meters which only require small blood samples exist, frequent measurements of the glucose level in blood samples taken from the patient are painful and not suited for a continuous monitoring.

U.S. Pat. No. 4,509,531 discloses a non-invasive watch-like monitoring device that measures body temperature and skin resistance. In the event of either a predetermined change in galvanic skin resistance or a predetermined change in peripheral skin temperature an alarm is generated which can waken a sleeper wearing the monitoring device.

Another watch-like device that uses perspiration and a drop in skin temperature to detect hypoglycaemia is the Sleep Sentry by Diabetes Sentry Products Inc. Studies for this device have shown that, when hypoglycaemia was confirmed to be present, the alarm was generated about 90% of the time, thereby leaving about 10% of the occurrences undetected. Furthermore, it is not uncommon for patients to experience a false alarm.

Hence, in the light of the above prior art devices it is desirable to increase the reliability of the hypoglycaemia detection.

International patent application WO 02/069798 discloses a method of determining the presence of a physiological condition in a person where the person's skin impedance, heart rate, QT interval and mean or peak frequency of the α wave are measured. The measured input data are fed into a multilayer feedforward neural network which is trained to calculate the patient's blood glucose status. The neural network is trained using the back-propagation algorithm in which synaptic strengths are systematically modified so that the response of the network approximates the blood glucose status of the patient with increasing accuracy.

It is a problem of the above prior art system that the actual performance of the neural network can only be assessed based on statistical methods. Hence, an explicit validation of the output for all possible sets of input data is unfeasible. However, since such a system is used in a medical context, it is desirable to provide a system with a reliability which may be systematically validated over the entire range of measured sensor values.

It is a further problem of the above prior art method that the back-propagation algorithm is time-consuming.

SUMMARY OF THE INVENTION

It is an object of the present invention to provide an apparatus for detecting a physiological condition in a person with a high reliability and a performance that can systematically be validated.

The above and other objects are achieved by an apparatus for detecting a physiological condition in a person, the apparatus comprising processing means adapted to receive at least two physiological parameters, and to determine, from the received physiological parameters, a result signal indicative of the presence or onset of said physiological condition; and output means for generating an output indicative of the result signal;

wherein the apparatus comprises storage means for storing a look-up table comprising a plurality of entries, each entry corresponding to a pre-calculated probability of the presence or onset of said physiological condition, the pre-calculated probabilities being determined by means of a mathematical process from previously monitored physiological parameters; and the processing means is adapted to process the received at least two physiological parameters to identify one of the plurality of entries of the look-up table, and to determine said result signal from the identified entry of the look-up table.

Consequently, by providing a look-up table such that any combination of sensor inputs is associated with one entry in the look-up table, and by using a suitable mathematical process such as a reinforcement learning algorithm to update the table values, an improved apparatus for detecting a physiological condition is provided.

In particular, it is an advantage that the entries stored in the look-up table may systematically be validated. Since any combination of inputs is associated with an entry in the look-up table, the output generated by the device for any combination of inputs may easily be validated. Furthermore, as the entries correspond to pre-calculated probabilities of the presence of said physiological condition that are determined by means of a mathematical process from previously monitored physiological parameters, a high reliability of the detection of the physiological condition is achieved.

Furthermore, is an advantage that the look-up table provides a direct indication of the probability of the presence or onset of said physiological condition indexed by the input parameters. Hence, the calculation/evaluation of complex physiological models or predictions of future blood glucose levels during operation is avoided, thereby providing a simple and reliable system.

It has been realised by the inventors that a high degree of reliability may be achieved with look-up tables of moderate sizes, thereby allowing an easy and systematic validation of all entries of the look-up table. For small look-up tables, a validation may even be performed manually.

In particular, it is an advantage that the apparatus automatically detects nightly hypoglycaemia for diabetic patients, sufficiently early for the patient to handle the problem himself/herself. In one embodiment, the physiological parameters are received as corresponding one or more sensor signals. For example, a patient may wear a set of sensors during the night. The sensor signals may be sent to a receiver of a central unit via a wireless connection. This central unit receives the signals, analyses them and sounds an acoustic alarm, if the analysis shows that the patient experiences a hypoglycaemia or is on the way to one.

It is a further advantage that the detection may be based on measurements of several secondary effects rather than a direct measurement of blood glucose.

Here, the term look-up table refers to any suitable data structure for storing a plurality of entries where each entry may be identified by a suitable index.

The term "detecting a physiological condition" is intended to comprise the detection of the presence/absence of such a condition and/or the onset of such a condition and/or a degree or severity to which such a condition is present.

The term "physiological parameter" comprises any quantitatively and/or qualitatively measurable parameter related to the physiological condition to be detected. Preferably, the physiological parameters are parameters that may be measured by non-invasive measurements. However, invasive measurements may be used as an input as well. When the parameters are measured automatically, they may be continuously or quasi-continuously monitored without the need for human interaction.

In the context of hypoglycaemia, examples of such parameters include heart rate/pulse, heart rate variability (HRV), skin impedance/perspiration, body/skin temperature, respiration frequency, respiration effort, eye movements, muscle tonus, parameters determined by an ECG, e.g. QT interval, parameters determined by Electroencephalography (EEG), e.g. the frequency of the α wave, a measurement obtained by an electro-oculogram (EOG), an $O_2$ saturation measurement, blood pressure, biosensors, or the like. The above parameters may be detected by any suitable known method. Preferably, the parameters are continuously or quasi-continuously sampled, thereby providing frequent updates of the measurements, e.g. one update every few seconds, every minute, or every few minutes.

By using more than one physiological parameter as an input to the detection apparatus, a high confidence level of the detection of the physiological condition is achieved, even though each one of the sensors per se may not be a good indicator of the presence or inset of the physiological condition. By combining two or more sensor signals, each of which carrying little information, the combined prediction provides a high degree of significance. This combination of sensor signals having comparatively low significance to a result signal of high significance will be referred to as sensor fusion.

In one embodiment, the physiological parameters further include one or more parameters measured by a third degree sensor. Here, the term third degree sensor comprises a sensor measuring a parameter that does not provide any direct information about the presence or absence of the physiological condition. Nevertheless, such a sensor may support the other sensor signals and provide an increased confidence level of the result. For example, in the context of hypoglycaemia, the $CO_2$ content of the blood is an example of such a third degree sensor signal. The $CO_2$ content provides an indication of whether the person is dreaming and/or sleeping restlessly, i.e. an indication of the presence of alternative causes of the other measured parameters, such as perspiration and eye movement, skin temperature, etc., thereby improving the reliability of the detection of hypoglycaemia and, in particular, reducing the number of false positive alarms.

Another option is to combine the above sensors with a first degree sensor, i.e. a sensor which directly measures a single quantity reflecting the physiological condition. In the context of hypoglycaemia, a non-invasive blood glucose measurement (BGM) such as infrared BGM may not be sufficiently accurate per se to be used as a BGM device, especially not for low blood glucose values. Hence, the infrared BGM may not be accurate enough to be used for a reliable detection of hypoglycaemia. However, in connection with one or more of the above, so-called second degree, sensors, an unreliable first degree measurement may contribute to an overall reliable detection.

The measured sensor signals may be received as an electrical signal from the respective sensors, e.g. via wires connected to the detection device. Alternatively or additionally, some or all of the sensor signals may be received via wireless data communication. For example, a sensor may include a radio transmitter for transmitting the measured parameter(s) via a short range radio communications link to a corresponding radio receiver in the detection device, thereby avoiding the need for wires connecting the different sensors with the detection device. In yet another embodiment, some or all of the sensors are integrated into the detection device, e.g. when the detection device is worn by the patient such that it has direct contact with the patient's skin, e.g. around the patient's wrist. Hence, the apparatus preferably comprises suitable input means for receiving the physiological parameters, e.g. any suitable circuitry or device adapted to receive a sensor signal.

Hence, the device may be worn by the patient, e.g. around the patient's wrist, or the device may be positioned in the proximity of the patient or in the proximity of a person caring for the patient, e.g. on a table next to the patient's bed.

The term "mathematical process" is intended to comprise any suitable algorithm for analysing previously measured data to determine suitable relations between the measured input values and the corresponding probabilities of the actual presence or onset of the physiological condition. For example, the mathematical process may comprise a statistical correlation analysis and/or a pattern analysis process of the measured sensor inputs and actual detected occurrences of the physiological condition. When the mathematical process comprises an adaptive learning algorithm, the generated entries of the look-up table may be adjusted during the actual usage of the device based on feedback provided by the user. Hence, the apparatus starts as pre-learned and can adapt to the user from there. When the adaptive learning algorithm comprises a reinforcement learning process, a particularly efficient data analysis with a high learning rate is achieved.

It is an advantage that the apparatus is adaptive with a high learning rate requiring only few interactions with the user in order to get a high degree of adaptation.

It is a further advantage that the apparatus may be initialised with a pre-learned look-up table. Consequently, when the user uses the apparatus for the first time it already has values that suits the user fairly well. Hence, the user needs to spend less time before getting to the point, where the apparatus is fully adapted.

It is a further example, that the actual function of the look-up table is much more transparent than for example multilayer neural networks, thereby facilitating a validation of the entire apparatus.

Furthermore, it is an advantage that the actual computation is less demanding than back-propagation neural networks and, therefore, faster.

Furthermore, the use of a look-up table avoids the problem of over-fitting which may arise when using multilayer back-propagation neural networks.

In a preferred embodiment, the apparatus further comprises input means for receiving a user input indicative of the presence or absence of said physiological condition and/or input means for receiving a measured quantity indicative of the presence of the physiological condition, e.g. a measured blood glucose level. Consequently, the user may provide feedback to the apparatus indicating whether an alarm generated by the apparatus was a false alarm and/or whether an alarm should have been generated and/or the like. Hence, the adaptive learning process may be updated based on the above feedback, thereby providing an improved performance adapted to the physiology of the individual patient. The input means for receiving a user input may comprise a keyboard, a touch screen, a keypad, a number of push buttons or other touch-sensitive input device, a voice/sound input device, or any other suitable input device.

Consequently, in a preferred embodiment, the processing means is further adapted to update at least the identified entry of the look-up table according to the adaptive process and in response to a user input indicative of the presence or absence of said physiological condition and/or a received measured quantity indicative of the presence of the physiological condition. Hence, the entry selected by the current sensor signal is updated based on the received feedback to better reflect the physiology of the patient and to improve the reliability of future detections. For example, if an alarm is classified as a false alarm by the user, the probability stored in the currently selected entry of the look-up table may be decreased by a predetermined value. Likewise, if the user has indicated that an alarm should have been generated, the corresponding probability may be increased. In one embodiment, all entries selected within a predetermined period prior to an alarm are updated, thereby increasing the efficiency of the algorithm.

In a preferred embodiment, the processing means is further adapted to discretize the received physiological parameters to obtain one of a plurality of possible combinations of discrete physiological parameters, each of the plurality of combinations being associated to a corresponding one of the plurality of entries of the look-up table. In particular, in one embodiment, the processing means is adapted to discretize the received physiological parameters by identifying, for each of the received physiological parameters, one of a corresponding number of intervals in which the received physiological parameter is determined to fall; resulting in a combination of identified intervals, the combination identifying a corresponding entry in the look-up table.

Hence, an efficient generation of an index for the look-up table is provided which may easily be validated and which does not require many computational resources.

Preferably, the processing of the received at least two physiological parameters to identify one of the plurality of entries of the look-up table results in a suitable index for the look-up table. In a preferred embodiment, the measured sensor signals are discretized with respect to a small number of intervals, thereby reducing the index space of the look-up table and, thus, reducing the complexity of the detection system. On the other hand the number of intervals is preferably selected large enough to provide a sufficient resolution to detect changes indicative of the onset or presence of the physiological condition. In one embodiment, each measured sensor signal is assigned to one of 2-10 intervals, preferably 3-6 intervals, more preferably 3-5 intervals, most preferably 4 intervals. However, it is understood that in some embodiments larger numbers of intervals may be desirable. It is understood that different numbers of intervals may be used for different sensor signals. Preferably, the intervals are selected to provide a higher resolution of the discretization at ranges that are significant for the physiological condition in question than at ranges which are less significant. Hence, preferably the intervals for at least some of the sensors are distributed asymmetrically around a normal value of a given sensor signal, i.e. around a value of the sensor signal corresponding to a normal physiological condition. In particular, the intervals are distributed such that there are a larger number of intervals on one side of the normal value than on the other side. It has been realised by the inventors that for many sensor signals both the frequency of occurrences as well as the degree of importance of the values for the determination of a physiological condition is asymmetrically distributed. Hence, by selecting asymmetrically distributed intervals, the number of required intervals and, consequently, the size of the look-up table are reduced.

Likewise, the number of different sensor signals should be selected large enough to provide a reliable detection and small enough to provide a small look-up table which can easily be validated. In a preferred embodiment, the at least two physiological parameters consist of 2-10 parameters, preferably 3-6 parameters, more preferably 4-5 parameters.

In a preferred embodiment, the apparatus further detects the rate of change of at least one of the physiological parameters, thereby further increasing the detection reliability.

The term processing means comprises any suitable circuit or device for processing data, e.g. a general- or special-purpose programmable microprocessor, a Digital Signal Processors (DSP), an Application Specific Integrated Circuits (ASIC), a central processing unit (CPU) of a computer, or the like.

The output means comprises any circuit or device for generating an output signal suitable for catching a user's or another person's attention, preferably suitable to wake up a sleeping user. Examples of such output means include a sound generator, a loudspeaker, a beeper, a vibrator, a light source, e.g. for generating a strong blinking light, etc. or any combination of the above. Additionally or alternatively, the alarm may be connected to a telecommunications system. Hence, if the physiological condition is detected, the detection apparatus may automatically dial a preselected number if there is no reaction to the alarm within a set timeframe.

The term storage means comprises any suitable circuit or device for storing data, for example an electrically erasable programmable read only memory (EEPROM), erasable programmable read only memory (EPROM), a random access memory (RAM), magnetic storage such as a hard disk, a removable storage medium, e.g. a memory card, a PCMCIA card, a smart card, or the like.

For example, the apparatus may comprise a suitably programmed and/or configured data processing device, e.g. a dedicated or multi-purpose medical device, a personal computer, a handheld computer, a PDA, a mobile terminal, or the like.

Further preferred embodiments are disclosed in the dependant claims.

The present invention can be implemented in different ways including the apparatus described above and in the following, a method, and further product means, each yielding one or more of the benefits and advantages described in connection with the first-mentioned method, and each having one or more preferred embodiments corresponding to the preferred embodiments described in connection with the first-mentioned apparatus and disclosed in the dependant claims.

The invention further relates to a method of alerting a patient to the risk of the presence of a physiological condition, the method comprising
  receiving at least two physiological parameters;
  determining, from the received physiological parameters, a result signal indicative of the presence of said physiological condition;
  notifying the patient in response to the result signal;
  wherein the step of determining the result signal comprises
    processing the received at least two physiological parameters to identify one of a plurality of entries of a look-up table, each entry of the look-up up table corresponding to a calculated probability of the presence of said physiological condition; and
    determining said result signal from the identified entry of the look-up table.

It is noted that the features of the method described above and in the following may be implemented in software and carried out in a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention further relates to a data processing system adapted to perform the method described above and in the following.

The invention further relates to a computer program comprising program code means for performing all the steps of the method described above and in the following when said program is run on a computer.

The invention further relates to a computer program product comprising program code means stored on a computer readable medium for performing the method described above and in the following when said computer program product is run on a computer.

BRIEF DESCRIPTION OF THE FIGURES

The invention will be explained more fully below in connection with a preferred embodiment and with reference to the drawing, in which.

DETAILED DESCRIPTION OF PREFERRED EMBODIMENTS

Figure 1A:
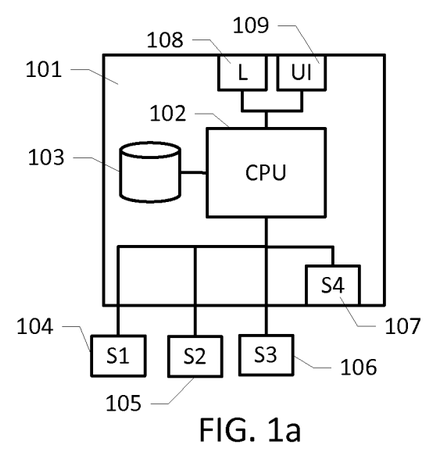
FIGS. 1a-c show block diagrams of examples of an apparatus for detecting hypoglycaemia.
Figure 1B:
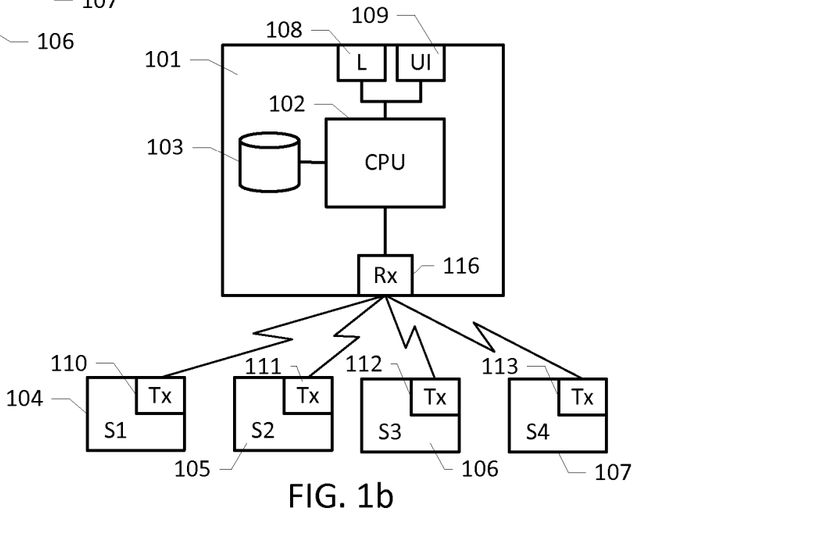
Figure 1C:
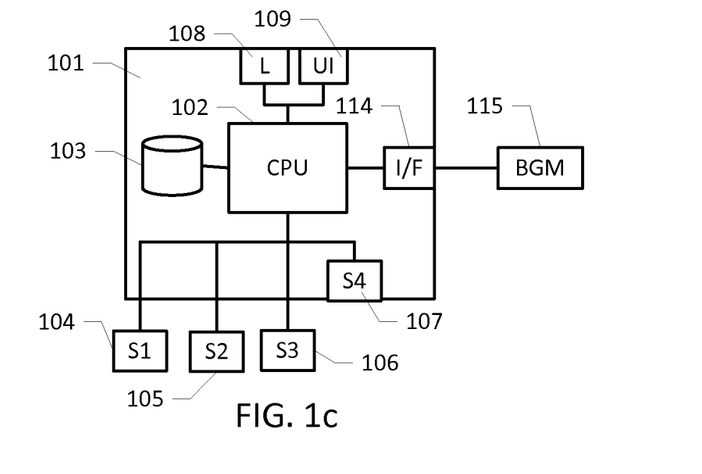

FIGS. 1a-c show block diagrams of examples of an apparatus for detecting hypoglycaemia. In the following, same reference numbers refer to the same components.

Referring to FIG. 1a, the apparatus 101 comprises a processing unit 102 a memory 103, a loudspeaker 108, and a user interface 109. The apparatus further comprises or is connected to a number of sensors generally designated 104, 105, 106, and 107. In the example of FIG. 1a, the apparatus 101 is connected to three sensors 104, 105, and 106 via cables, and the apparatus 101 further comprises an integrated sensor 107, e.g. a pulse sensor or a skin temperature sensor integrated into a device, e.g. a device which is worn around the user's wrist.

For example, the sensors 104, 105, 106, and 107 may measure the pulse, the heart rate variability, the skin temperature, and the skin impedance, respectively. However it is understood that alternatively or additionally other measurements may be performed.

The pulse sensor may be based on any suitable method known in the art such as photoelectric measurements, e.g. as described in "The Biomedical Engineering Handbook, CRC Press, Volume 1 (ISBN: 0-8493-0461-X), p. 86-1-86-7. For example, the pulse sensor may be a pulse oximeter, e.g. placed at the user's fingertip or ear lobe.

The skin impedance may be based on any suitable method known in the art. For example, the skin impedance sensor may comprise a concentric type electrode with an outer passive electrode and an inner electrode, e.g. as disclosed in WO 02/069798.

The measurement of the hart rate variability (HRV) may be based on any suitable method known in the art, e.g. as described in "The Biomedical Engineering Handbook, CRC Press, Volume 1 (ISBN: 0-8493-0461-X), p. 13-1-13-8. For example, the HRV may be determined based on an ECG, e.g. measured via electrodes placed on the user's chest and/or arms.

The skin temperature may be measured based on any suitable method known in the art, e.g. by means of a thermistor-based sensor.

It is understood that in alternative embodiments a different set of sensor signals may be used. In addition or alternatively to the above sensor signals such a set of sensor signals may include respiration frequency, respiration effort, eye movements, EOG, muscle tonus, parameters determined by an ECG, e.g. QT interval, frequency of the α wave, etc., parameters determined by Electroencephalography (EEG), etc, third degree sensor signals such as the $O_2$ and/or $CO_2$ content of the blood, first degree sensor signals such as a non-invasive blood glucose measurement, etc., or any combination of the above. The above parameters may be detected by any suitable method known per se in the art.

The sensors 104, 105, 106, and 107 forward the measured sensor signals to the processing unit 102. In one embodiment, the signals are forwarded as analogue signals which are processed by the processing unit, e.g. by sampling/digitizing the analogue signal and/or averaging the signals over a predetermined time, and/or the like. In another embodiment, some or all of the sensors 104, 105, 106, and 107 perform some or all of the above processing and forward a suitably sampled, averaged and digitized signal to the processing unit 102.

The processing unit 102 determines an entry of a look-up table from the combination of sensor signals, retrieves the identified entry from a look-up table stored in the memory 103, and determines, based on the retrieved entry, whether or not an alarm should be raised, as will be described in greater detail below.

If an alarm is raised, the processing unit activates the loudspeaker 108. It is understood that alternatively or additionally, any other suitable output device for generating an alarm may be used.

The apparatus further comprises a user interface 109, e.g. one or more push buttons, a keypad, a touch screen, or the like, allowing the user to provide feedback to the apparatus. For example, the user interface may comprise a button for turning off the alarm and further buttons or a keypad for providing additional feedback, e.g. an acknowledgment that the alarm was a justified alarm or the alarm was a false alarm, i.e. whether the user actually experiences hypoglycaemia. This feedback may then be used in order to adaptively modify one or more entries in the look-up table as described in greater detail below. The user interface may further allow a user to enter a measured blood glucose level, thereby providing a feedback about the degree of hypoglycaemia, if any.

FIG. 1b shows another example of an apparatus for detecting hypoglycaemia. In this example, the apparatus 101 receives the sensor signals from the sensors 104, 105, 106, and 107 via radio communications. Consequently, the apparatus 101 further comprises a short-range radio receiver 116, e.g. a receiver adapted to receive radio signals in an unlicensed radio frequency band. In one embodiment, the receiver is implemented according to the Bluetooth standard. Similarly the sensors 104, 105, 106, and 107 each comprise a corresponding radio transmitter 110, 111, 112, and 113, respectively, adapted to communicate with the receiver 116.

For example, the apparatus 101 with the receiver, the processing unit and the alarm output may be a device that may be placed on a night stand or it may be a watch-like unit worn around the user's wrist. In case of the nightstand device, the device may optionally include a refrigerators compartment that is sufficiently large to hold some juice, a soft drink, or the like, thereby allowing the patient to immediately counterbalance a condition of hypoglycaemia in case of an alarm.

FIG. 1c shows yet another example of an apparatus for detecting hypoglycaemia. In this example, the apparatus 101 is connected to three sensors 104, 105, and 106 via cables, and the apparatus 101 further comprises an integrated sensor 107, as in the example of FIG. 1a. Additionally, the apparatus of FIG. 1c further comprises an interface circuit 114 for receiving a signal from a blood glucose measurement device 115. For example, the interface circuit may be a wired connection, a plug-and-socket connection or a wireless connection, e.g. an infrared or radio-based connection. The interface circuit 114 allows a user to directly transfer a blood glucose value measured by the measurement device 115 to the apparatus 101, thereby allowing the user to verify or reject an alarm raised by the apparatus 101.

It is understood that a number of equivalent embodiments of an apparatus may be designed, including combinations of the above examples.

Figures 2, 3:
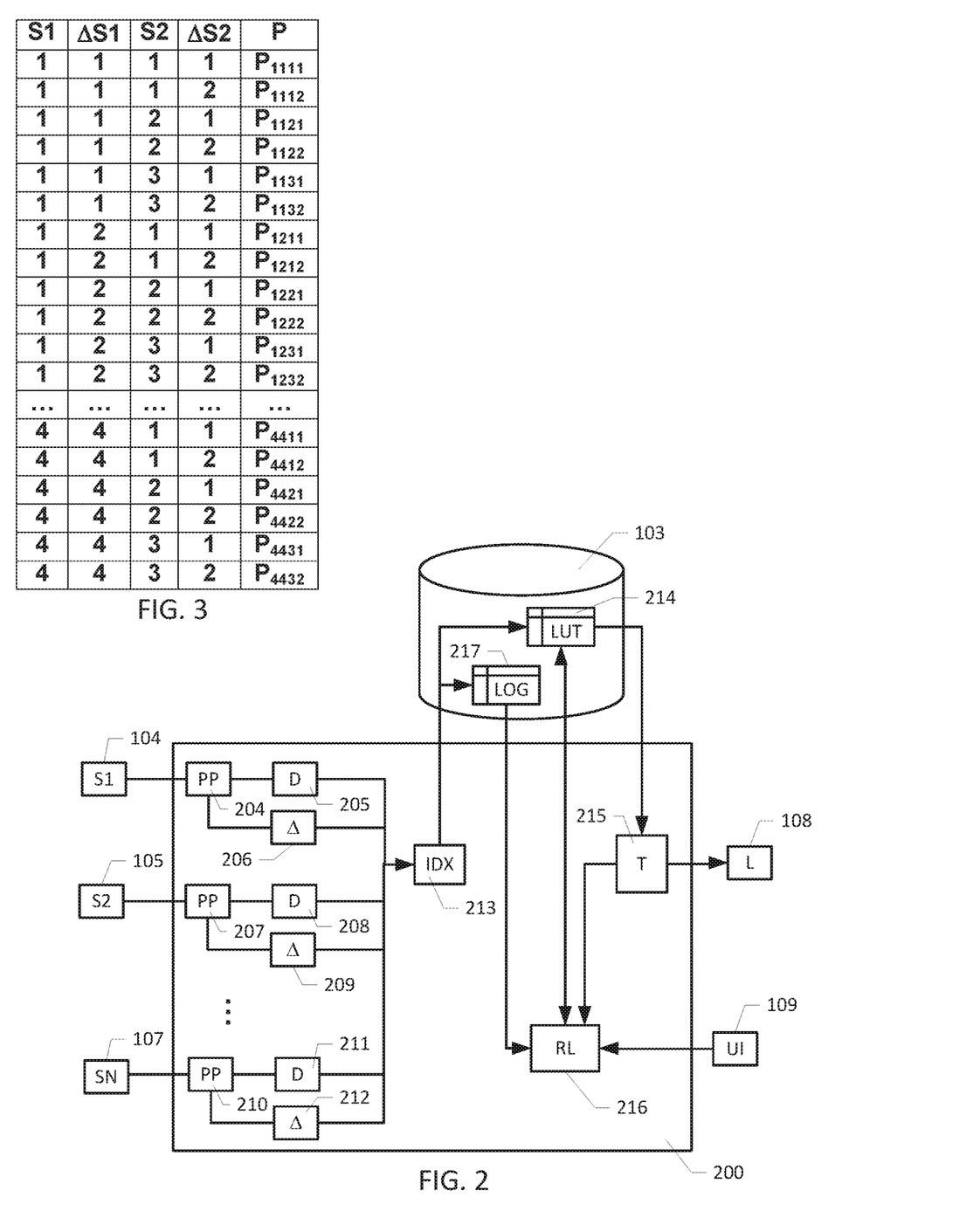
FIG. 2 shows a more detailed block diagram of the functions performed by the processing unit of an apparatus for detecting hypoglycaemia.
FIG. 3 shows an example of a look-up table comprising probabilities for the presence or onset of hypoglycaemia.

FIG. 2 shows a more detailed block diagram of the functions performed by the processing unit of an apparatus for detecting hypoglycaemia.

The processing unit 200 receives inputs from N sensors exemplified by sensors 104, 105, and 107, generally designated S1, S2, . . . , SN.

The signal received from sensor S1 is fed into a pre-processor module 204 where it is suitably pre-processed, e.g. averaged over a predetermined time period, e.g. a few seconds, and/or normalised and/or the like. The pre-processed signal is fed into a discretizer module 205. The discretizer module 205 determines in which of a number of predetermined intervals the received sensor signal falls. Assuming that the total range of the sensor signal S1 lies between $S1_{min}$ and $S1_{max}$, the range is divided into K1 intervals $I_{1,1}=(S1_{min};S1_1]$, $I_{1,2}=(S1_1;S1_2]$, . . . , $I_{1,K1}=(S1_{K1-1};S1_{max})$, and the discretizer module determines the interval $I_{1,k}=(S1_{k-1};S1_k]$, such that $S1_{k-1}<S1 \le S1_k$. For example, skin temperature T may be discretized as "quite low" (corresponding to T≤23° C.), "low" (23° C.<T≤25° C.), "normal" (25° C.<T≤27° C.), and "high" (T>27° C.). Hence, the normal value (26° C.) is in the third interval and the intervals are shifted towards the temperature range which is relevant for the detection of hypoglycaemia, i.e. towards the temperatures below the normal value. The discretizer outputs the number of the identified interval.

The pre-processed signal is also fed into a module 206 for determining a rate of change of the sensor signal S1. Similarly to the discretization of the actual sensor signal, the rate of change is also determined as falling within one of a number of intervals. In one embodiment, the range of change may simply be determined as a difference of two consecutive values of the sensor signal. For example, in the above example of skin temperature, the rate of change may be discretized into "rapidly decreasing", "slowly decreasing", "slowly increasing", rapidly increasing." The module 206 outputs an indication of the rate of change, e.g. by outputting the number of the corresponding interval.

Similarly, the sensor signal received from sensor S2 is pre-processed in pre-processor 207, discretised in discretizer module 208, and a rate of change is determined in module 209. The sensor signal received from sensor SN is pre-processed in pre-processor 210, discretised in discretizer module 211, and a rate of change is determined in module 212. hence, in this embodiment, 2N interval numbers are generated.

The index numbers determined from the received sensor signals and the corresponding rates of changes are fed into the index module 213. For each possible combination of the 2N intervals, the index module determines a corresponding entry in the look-up table 214. The look-up table is stored in a memory 103, e.g. an EPROM, EEPROM, a hard disk, a memory card, or the like. Each entry of the look-up table corresponds to an estimated probability that the patient is hypoglycaemic. The index module further stores the determined index number together with a corresponding time-stamp in a log table 217 stored in the memory 103 or, alternatively, in a separate memory. For example, the log table may store the index numbers selected during the past 12 hours, the last 24 hours, or the like.

The determined probability retrieved from the look-up table 214 is fed into the threshold module 215, where the probability is compared to a predetermined threshold. For example, the threshold may be preset by a physician for the individual patient. Preferably, a single global threshold is used for all entries of the look-up table, thereby reducing the number of parameters that have to be adjusted. If the threshold module determines that the probability is below the threshold, no alarm is generated. Otherwise, if the probability is determined to be above the threshold an alarm signal is output by the processing unit controlling the loudspeaker 108 to sound an audible alarm. The threshold module further forwards a signal to a reinforcement module 216 indicating that an alarm has been triggered.

In one embodiment, the above process is repeated in regular time intervals, e.g. every 30 seconds, every minute, every few minutes, or the like. Consequently, in this embodiment, the sensors acquire measurements over one time interval, and the resulting signal is processed, transformed into an index for the look-up table, and from the corresponding probability it is determined whether or not an alarm is to be raised. In some embodiments, an alarm is only raised, if the determined probability is determined to be above threshold in a predetermined number of consecutive time intervals.

If the processing unit receives a signal from the user interface relating to the actual physiological condition of the user, the received information is fed into a reinforcement learning module 216. Based on the received input and any possible signals received from the threshold unit about any triggered alarms, the reinforcement module determines a time period such that all entries of the look-up table selected during that time period are modified. For example, if an alarm has been generated by the apparatus and if the user has indicated via the user interface 109 that the alarm was a false alarm, the reinforcement module may determined to decrease all probabilities that were selected during the last 30 minutes prior to the alarm. Likewise, if an alarm has been generated by the apparatus and if the user has acknowledged via the user interface 109 that he/she actually experiences a condition of hypoglycaemia, e.g. based on a blood glucose measurement, the reinforcement module may determined to increase all probabilities that were selected during the last 30 minutes prior to the alarm. Similarly, if the received user input indicates that the user has had an undetected condition of hypoglycaemia sometime during the previous night, the reinforcement module may determine to modify all entries of the look-up table 214 that were selected during the previous night. Consequently, the reinforcement module retrieves information from the memory 217 identifying the entries that were selected during the determined period of time and the corresponding points in time at which the entries were selected. The reinforcement module 216 then calculates modified probabilities for the identified entries and stores the modified probabilities in look-up table 214. An embodiment of the update algorithm will be described below.

It is understood, that the functions performed by the processing unit and described with reference to FIG. 2 above may be implemented fully or partly in software, where the blocks in FIG. 2 represent different functional components.

FIG. 3 shows an example of a look-up table comprising probabilities for the presence or onset of hypoglycaemia. For simplicity, in the example of FIG. 3 it is assumed that the corresponding apparatus receives signals from two sensors S1 and S2. It is further assumed that the signal from S1 is discretized into four intervals indexed 1, 2, 3, and 4, while the signal from S2 is discretized into three intervals indexed 1, 2, and 3. Furthermore, the rate of change of signal S1, labelled ΔS1, is dicretized in four intervals indexed 1, 2, 3, and 4, while the rate of change of signal S2, labelled ΔS2, is discretized in two intervals indexed 1 and 2. Each row of the look-up table of FIG. 3 corresponds to one of the possible combinations of intervals of S1, ΔS1, S2, and ΔS2, and each row includes an entry comprising a probability P assigned to the corresponding combination of intervals. In FIG. 3, the probability values are schematically indicated by $P_{ijkl}$, where $i \in \{1,2,3,4\}$, $j \in \{1,2,3,4\}$, $k \in \{1,2,3\}$, $l \in \{1,2\}$ correspond to the indices of the intervals corresponding to S1, ΔS1, S2, and ΔS2, respectively. Hence, the look-up table in this example comprises 4*4*3*2=96 entries. It will be appreciated that the size of the look-up table rapidly increases with the number of sensors and with the number of intervals for each sensor. Hence, it is preferred that the number of sensor signals and the respective numbers of intervals are selected to be small but still large enough to provide a reliable detection of the physiological condition. For hypoglycaemia it is preferred to use between 2 and 7 intervals for each sensor signal and each rate of change, preferably 4 intervals. It will further be appreciated that the format of the data structure in which the look-up table is stored may vary depending on the actual implementation. For example, the table may be stored as a multi-dimensional array, as a hierarchical tree structure, or the like.

Figure 4:
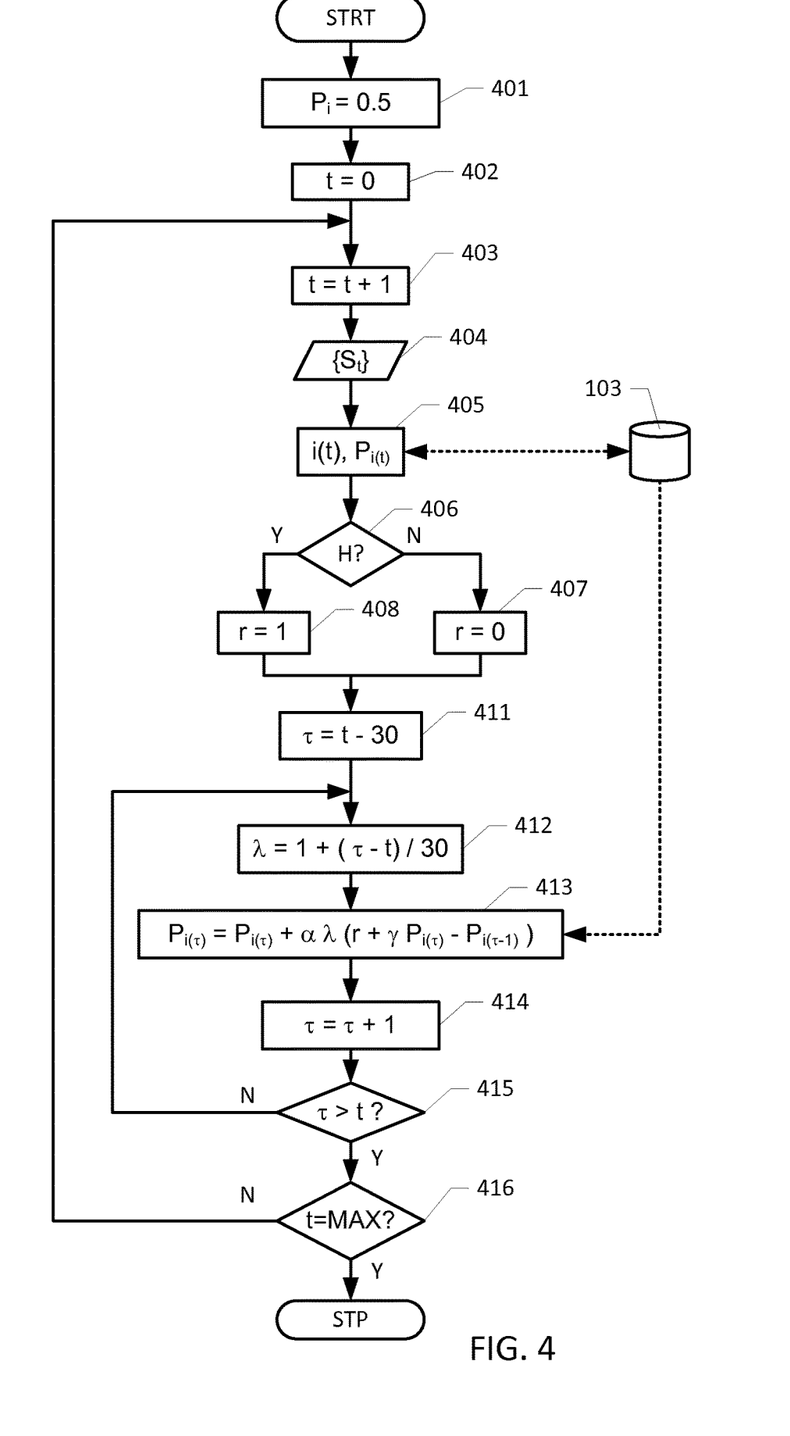
FIG. 4 shows a flow diagram of a method of determining the entries of the look-up table based on reinforcement learning.

FIG. 4 shows a flow diagram of a method of determining the entries of the look-up table based on reinforcement learning.

The process is based on a set of experimental data comprising measured sensor signals for a patient over a predetermined period of time, e.g. a few days, a week, or even longer, and corresponding indications whether the patient was in a condition of hypoglycaemia or not. Preferably, the experimental data is obtained for the same patient who subsequently will use the apparatus, thereby providing an individualised look-up table. Alternatively, the look-up table may be pre-trained based on generic patient data, thereby avoiding a data acquisition for each individual patient. In the following it is assumed that the data is represented as a sequence of data records, each data record comprising a time t, a set of measured sensor signals $\{S_t\}$ at time t, e.g. sensor signals averaged over a time period around the time t, and an indication whether the patient at time t was in a state of hypoglycaemia or not. In the following, it is further assumed that the time is incremented by 1 minute, i.e. that there is one data record per minute, and that the data records are labelled by t=1,2,3, . . . , MAX, where MAX corresponds to the number of records in the data set. For example, the above data may be obtained during an overnight monitoring of a patient under supervision. It is understood that a different time increment may be used instead, e.g. any increment between a few seconds and several minutes.

In an initial step 401, all entries of the look-up table are initialised to 0.5, i.e. $P_i=0.5$ for probabilities $P_i$. Here the probabilities are assumed to be indexed by i.

In step 402, an iteration is started. For simplicity, it is assumed that the time is initialised at t=0, and the steps from step 403 through step 416 are iterated until all data records for all times t are processed, i.e. until t=MAX.

In step 403 the time t is incremented, i.e. t←t+1.

In step 404, the process retrieves the sensor signals $\{S_t\}$ for time t from memory and, in step 405, the corresponding index i(t) identifying one of the entries of the look-up table is determined as was described above. From the look-up table, the corresponding probability $P_{i(t)}$ is retrieved from the look-up table stored in the memory 103. The identified index i(t) and the corresponding time t are stored in a suitable data record in memory 103 for later use.

At step 406 the process determines from the corresponding data record whether there actually was a condition of hypoglycaemia at time t. If no such condition was present at time t, the process continues at step 407 where a reinforcement parameter r is set to r=0. Otherwise, i.e. if a condition of hypoglycaemia was present, the process continues at step 408 where the reinforcement parameter r is set to r=+1. Subsequently, the process continues at step 411.

At step 411, i.e. after setting the reinforcement parameter, the process enters a loop. The loop comprises the steps from step 412 through step 415 and performs an update of the probabilities of all the entries of the look-up table that have been identified during a predetermined period prior to the current time t. In the embodiment of FIG. 4, the predetermined period of time is assumed to be 30 minutes. Consequently, before entering the loop, i.e. at step 411, a counter τ is set to τ=t−30, i.e. to the beginning of the predetermined period. It is understood that if τ<1, τ is set to 1 instead.

In step 412, a weighting parameter λ is set to $$\lambda = 1 + (\tau - t)/30,$$

i.e. the parameter λ is linearly increased from λ=0 at time t−30 to λ=1 at time t, corresponding to the observation that the correlation between the physiological state of the patient at time τ and the state at time t decreases with increasing difference t−τ. It is understood that other functional forms of a gradual increase may be used instead.

At step 413, the entry of the look-up table that was selected at time τ, i.e. the entry with index i(τ) as retrieved from the data record in memory 103, is updated according to $$P_{i(\tau)} = P_{i(\tau)} + \alpha\lambda(r + \gamma P_{i(\tau)} - P_{i(\tau-1)}),$$

i.e. the probability is adjusted by the correction term $$\Delta P_\tau = \alpha\lambda(r + \gamma P_{i(\tau)} - P_{i(\tau-1)}).$$

Hence, the correction depends on the probabilities at time τ and at time τ−1. The parameter γ determines the relative weight of the probabilities at time τ and at time τ−1. Preferably the value of γ is selected according to the sampling rate and the length of the time period. For example for a time period of 30 minutes and a sampling once a minute as in the current example, values of γ between 0.97 and 0.98 are preferred. However, other values may be used as well. The parameter α is referred to as the learning rate and determines the overall strength of the correction. For example, the learning rate may be selected to be between 0.4 and 0.6. However, other values may be selected as well. The learning rate is multiplied with the factor λ, thereby causing the most recent entries prior to the false positive or false negative result to be corrected by the largest correction factors. Finally, the parameter r is the reinforcement parameter determined in steps 406-408.

For example, if the probabilities at time τ and at time τ−1 are equal, the term $\gamma P_{i(\tau)} - P_{\tau-1})$ is a small negative number. Hence, if r=0, the correction $\Delta P_\tau$ is a small negative number, and if r=1, the correction $\Delta P_\tau$ is a positive number. Hence, if r=0, i.e. if no hypoglycaemia was present at time t, the probability is slightly decreased. Otherwise, if hypoglycaemia was present, r=1, the probability is increased. It is noted that the resulting probability $P_{i(\tau)}$ may be forced to fall in the interval [0;1] simply by setting $P_{i(\tau)}=0$ if $P_{i(\tau)}<0$ and to $P_{i(\tau)}=1$ if $P_{i(\tau)}>1$.

At step 414, the parameter τ is incremented, and at step 415 it is tested whether τ>t, i.e. whether the correction loop is completed. If τ>t, the process continues at step 416, otherwise the process returns to step 412.

At step 416 it is tested whether all data records have been processed, i.e. whether t=MAX. If all data records have been processed, the process terminates; otherwise the process returns to step 403 for iteration of the above steps at the subsequent time step t+1.

Hence, in the above, a process for determining an initial set of probabilities for the entries of the look-up table of an apparatus according to the invention is disclosed. In some embodiments, the entries of the look-up table are subsequently updated during operation based on feedback received from the patient, thereby providing an adaptive detection apparatus where the probabilities in the look-up table are both adaptive with respect to the individual patient and with respect to a development of the patient over time.

It is understood that, alternatively or additionally, other methods for determining the initial set of probabilities may be used.

For example, a statistical correlation-analysis on the experimental data may be performed, e.g. using a statistics software package like SAS or MatLab. The analysis may be started with any pair of two sensor signals of the set of sensor signals. Starting with the pair that caries most information, additional signals from any of the other sensors or trends of the sensor signals may be added one by one in order to identify a set of signals with a high correlation to the observed hypoglycaemia events. This is an efficient but rather time consuming solution.

In another embodiment, one, more or all the sensor data and possibly also the trends from the experimental data set are analysed with a conventional pattern analysis software. The mapping from sensor signals to the presence or absence of a hypoglycaemia condition is saved and used without subsequent user adaptation.

Figure 5:
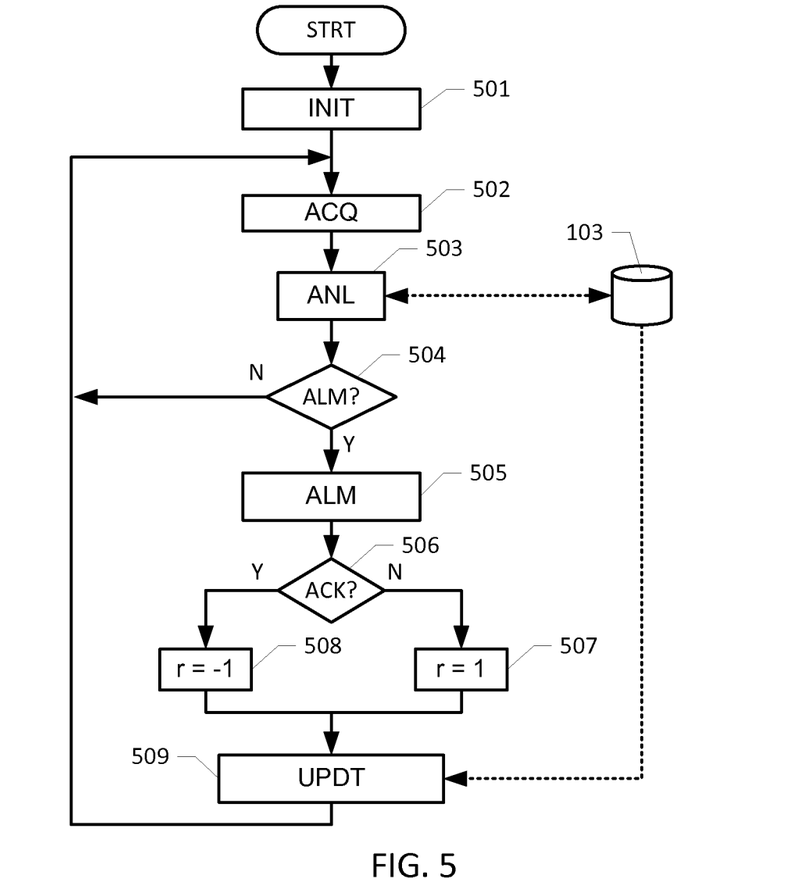
FIG. 5 shows a flow diagram of the process of a daily or nightly operation of a detection apparatus including an on-line adaptation of the entries of the look-up table.

FIG. 5 shows a flow diagram of the process of a daily or nightly operation of a detection apparatus including an on-line adaptation of the entries of the look-up table.

In an initial step 501, the apparatus is initialised. After placing the sensors at the correct positions on the patient's body and connecting any wires if necessary, the apparatus is put in an initialisation state, e.g. by powering on the apparatus. Preferably, during the first couple of minutes while the patient is wearing the sensors, the patient should not have hypoglycaemia. During this period, the apparatus may check whether all sensor signals are received correctly, and acquire initial sensor signals, e.g. by sampling data over an initial time interval, thereby adapting to the physiology of the user.

After the initialisation step, the sensor signals are continuously or periodically acquired and analysed:

In step 502, the sensor signals are acquired by the sensors and forwarded to the apparatus, e.g. by sampling the sensor signals over a predetermined period, e.g. one minute.

In step 503, the acquired sensor signals are analysed by the apparatus, i.e. the sensor signals are discretized, the rates of change of the sensor signals are determined and discretized, and the entry of the look-up table that corresponds to the resulting combination of discretized sensor signals and rates of changes is identified, as was described in greater detail above. The index of the identified entry of the look-up table is stored in memory 103.

In step 504, the process compares the identified entry of the look-up table with a predetermined threshold and determines whether an alarm should be raised. If the probability is below threshold, no alarm is raised, and the process returns to step 502 starting the next sampling interval. If the probability is above threshold, the process continues at step 505. In some embodiments, an alarm is raised only if the probability is higher than the threshold during a predetermined number of consecutive intervals, e.g. 2-5 intervals, thereby reducing the risk of false alarms due to isolated erroneous measurements. For example, the number of consecutive intervals required may be selected by a physician or the user.

In step 505, the alarm is raised, e.g. by sounding an audible alarm and/or activating a vibrator and/or the like, thereby alerting the patient to a potential condition of hypoglycaemia.

In step 506, the process receives an acknowledgment from the patient. For example, the patient may press a button on the apparatus to stop the alarm. In some embodiments, if the process does not receive an acknowledgment of the alarm in a predetermined period of time, the process may increase the severity of the alarm, e.g. by increasing the volume of the alarm sound, by sending a control signal to a different device, e.g. in order to invoke an alarm in a different room of the house, or by causing a modem to dial a predetermined telephone number e.g. of a hospital, or the like, in order provide help to the patient.

In the following it is assumed, that the patient may either provide an affirmative acknowledgment confirming that the patient experiences a condition of hypoglycaemia, or the patient may provide a rejection of the alarm. In alternative embodiments, the patient may merely switch off the alarm without providing any feedback, thereby preventing the entries of the look-up table from being updated. In this case, the process would simply continue at step 502 after the alarm has been switched off. In yet another embodiment, the apparatus may comprise three buttons "Switch off alarm", "confirm alarm", and "reject alarm", thereby allowing the patient to decide whether or not to provide feedback for a given alarm. In yet another embodiment, the apparatus may be operated in two modes, an adaptive mode where feedback from the patient is accepted, and a stationary mode without adaptation of the probabilities.

If, in step 506, the process has received a confirmation of the alarm, the process sets a reinforcement parameter r to r=1 (step 507). Otherwise, if the process has received a rejection of the alarm, the process sets the reinforcement parameter r to r=-1 (step 508).

In some embodiments, the patient may measure the blood glucose level and enter the measured blood glucose level into the apparatus via a suitable user interface or via a data connection between the blood glucose measurement device and the hypoglycaemia detection apparatus. Hence, in this case the confirmation or rejection of the alarm may be replaced or supplemented with a measured blood glucose level. In this embodiment the reinforcement parameter may be determined from the measured blood glucose level BG, if such a measurement is provided. For example, in one embodiment r may be determined as follows: If the BG is measured to less than 3.5 mmol/l then r=1. If BG is measured in the interval 3.5-6 mmol/l, r is calculated to be r=(19-4 BG)/5, i.e. r depends linearly on the measured blood glucose level. For BG>6 mmol/l, r=-1. Hence, in this embodiment a continuous reinforcement parameter is determined.

After determining the reinforcement parameter r, the process continues at step 509, where the process updates all entries of the look-up table that were selected during a predetermined period $\Delta T$ prior to the time $t_{alarm}$ of the alarm, e.g $\Delta T$=30 minutes. The corresponding indices of the entries to be updated are retrieved from memory 103, and the entries are updated as described in connection with FIG. 4, i.e. they are updated by the correction term $$\Delta P_{\tau=\alpha\lambda(r+\gamma P_{i(\tau)}-P_{i(\tau-1)})},\ \forall\tau\in[t_{alarm}-\Delta T;\ t_{alarm}].$$

Here, the learning rate $\alpha$, the parameter $\gamma$, and the relative weight factor $\lambda$ are determined as described in connection with FIG. 4 above.

Subsequently, the process continues at step 502, i.e. by continuing the data acquisition and analysis.

In one embodiment, the discretized sensor data in memory 520 is saved for an entire night. For example, assuming a storage requirement of one byte per discretized sensor signal, 12 hours data of signals from 5 sensors and their corresponding discretized rates of changes with a sampling frequency of 1 sample/minute requires 2*5*60*12 bytes, i.e. approximately 8 kilobyte of data. If the apparatus receives a feedback from a patient indicating that an undetected hypoglycaemia has occurred during a predetermined period, e.g. at an unspecified time during the past six hours, or at an unspecified time during the last night, the apparatus may update all entries of the look-up table that were selected during that period of time, i.e. in a predetermined time interval $[t_0;t_1]$.

For example, all the entries selected during the specified time period may get their probabilities updated with $$\Delta P_{\tau=\alpha}(1+\gamma P_{i(\tau)}-P_{i(\tau-1)}),\ \forall\tau\in[t_0;\ t_1],$$

corresponding to a reinforcement parameter of r=1, and a relative weighting factor $\lambda$=1. Hence, all the probabilities in the predetermined time period are updated with the same relative strength, since the exact time within the time period at which the hypoglycaemia occurred is unknown.

Hence, if a patient wakes up in the morning or at some point during the night, and is aware of the fact that he/she has experienced hypoglycaemia at some point during the night, the patient may initiate the above update, e.g. by indicating the time interval via a suitable user interface.

The invention has mainly been described in connection with hypoglycaemia and the sensors relevant for the detection of hypoglycaemia. However, it is understood that the invention may also be applied to the detection of other physiological conditions, possibly based on other types of measurements.

Although preferred embodiments of the present invention have been described and shown, the invention is not restricted to them, but may also be embodied in other ways within the scope of the subject matter defined in the following claims.

For example, it is envisaged to improve the user's comfort by letting the bed sheets be part of the device, e.g. by placing some of the sensors, for example the sweat and temperature sensor, in the sheet. Some of the wires can also be placed in the sheet. For example, a heart rate variability analysis requires two connected sensors. The wire connecting these sensors may advantageously be put in the sheet.

It is further envisaged to combine the detection apparatus described herein with a glucagon dosing device. In such a combined system, in case no one reacts to the alarm generated by the detection apparatus, the detection apparatus may send a signal to the glucagon dosing device that injects the patient. For example, the signal may be sent via a wireless connection. The possibility of this depends on the development of durability of ready-to-use glucagon.

The invention claimed is:

1. A method of alerting a patient to the probability of the presence of hypoglycaemia, the method comprising:

receiving, via an input of an apparatus, at least two physiological parameters corresponding to a patient state at time $T_s$ from a group of physiological parameters comprising heart rate or pulse, heart rate variability, skin impedance, perspiration, body temperature, skin temperature, respiration frequency, respiration effort, eye movement, muscle tonus, a measurement obtained by electrooculogram (EOG), an oxygen saturation measurement, blood pressure, a carbon dioxide content of blood, and a non-invasive blood glucose measurement, and a blood glucose level;

using a processor of the apparatus, determining, from the at least two physiological parameters, a result signal indicative of the presence or onset of hypoglycaemia by processing the received physiological parameters to identify one of a plurality of entries of a look-up table, wherein each entry of the look-up up table begins as an initial set of pre-calculated probabilities of the presence or onset of hypoglycaemia, the pre-calculated probabilities being determined by an adaptive learning algorithm from previously monitored physiological parameters of the person;

wherein a loop begins with a counter τ at the beginning of a predetermined period of time and the at least two physiological parameters are modified by a weighting parameter λ, wherein the most recent physiological parameters are weighted more than the older physiological parameters wherein the counter τ is provided as:

$\tau = T_s - 30$ wherein the predetermined period of time is 30 minutes, and if τ<1, τ is set to 1 instead;

wherein the initial set of pre-calculated probabilities are adjusted by a correction term γ that determines the relative weight of the probabilities at time τ and at time τ−1;

wherein entries of the look-up table are subsequently updated during operation based on feedback received from the patient, thereby providing an adaptive detection apparatus where the probabilities in the look-up table are both adaptive with respect to the individual patient and with respect to a development of the patient over time; and generating a notification, using the apparatus, of the result signal indicative of the presence or onset of hypoglycaemia.

2. A method according to claim 1, further comprising receiving a measured quantity indicative of the presence of hypoglycaemia.

3. A method according to claim 2, wherein the measured quantity is a measured blood glucose level.

4. A method according to claim 1, wherein the weighting parameter λ is provided as:

$\tau = 1 + (\tau - T_s)/30$ wherein the predetermined period of time is 30 minutes and the weighting parameter λ is linearly increased from λ=0 at time $T_s$−30, to λ=1 at time $T_s$, wherein the most recent physiological parameters are weighted more than the older physiological parameters.

5. A method according to claim 1, wherein the probabilities are adjusted by the correction term γ modified by a learning rate a wherein the probability is adjusted according to the equation:

$\Delta P_\tau = P_{i(\tau)} + \alpha(r + \gamma P_{i(\tau)} - P_{i(\tau-1)})$ wherein the correction term γ determines the relative weight of the probabilities at time τ and at time τ−1 and has a value between 0.97 and 0.98, and the learning rate a determines the overall strength of the correction and has a value between 0.4 and 0.6.

6. A method for detecting a probability of hypoglycaemia in a person, the method comprising:

providing a storage device adapted to store a look-up table comprising a plurality of entries, wherein each entry is a pre-calculated probability of the presence or onset of hypoglycaemia and each entry begins as an initial set of pre-calculated probabilities, the pre-calculated probabilities being determined by an adaptive learning algorithm from previously monitored physiological parameters of the person corresponding to a patient state at time $T_s$;

providing a processor adapted to receive at least two physiological parameters and identify one of the plurality of entries of the look-up table, wherein the identification comprises comparison of at least two physiological parameters against stored values of the look-up table, and wherein the processor is further adapted to determine, from the received physiological parameters, a result signal indicative of the presence or onset of hypoglycaemia wherein the entries of the look-up table are subsequently updated during operation based on feedback received from the patient;

wherein a loop begins with a counter τ at the beginning of a predetermined period of time and the at least two physiological parameters are modified by a weighting parameter λ, wherein the most recent physiological parameters are weighted more than the older physiological parameters wherein the counter τ is provided as:

$\tau = T_s - 30$ wherein the predetermined period of time is 30 minutes, and if τ<1, τ is set to 1 instead;

wherein the initial set of pre-calculated probabilities are adjusted by a correction term γ that determines the relative weight of the probabilities at time τ and at time τ−1;

wherein entries of the look-up table are subsequently updated during operation based on feedback received from the patient, thereby providing an adaptive detection apparatus where the probabilities in the look-up table are both adaptive with respect to the individual patient and with respect to a development of the patient over time;

providing an output device adapted to generate an output indicative of the result signal corresponding to a pre-calculated probability of the presence or onset of hypoglycaemia;

receiving a user input indicative of the presence or absence of hypoglycaemia wherein the processor is further adapted to update at least the identified entry of the look-up table according to the adaptive learning algorithm process and in response to a user input indicative of the presence or absence of hypoglycaemia and/or a received measured quantity indicative of the presence of hypoglycaemia.

7. A method according to claim 6, wherein the adaptive learning algorithm comprises a reinforcement learning process.

8. A method according to claim 6, wherein the processor is further adapted to discretize the received physiological parameters to obtain one of a plurality of possible combinations of discrete physiological parameters, each of the plurality of combinations being associated to a corresponding one of the plurality of entries of the look-up table.

9. A method according to claim 8, wherein the processor is adapted to discretize the received physiological parameters by identifying, for each of the received physiological parameters, one of a corresponding number of intervals in which the received physiological parameter is determined to fall; resulting in a combination of identified intervals, the combination identifying a corresponding entry in the look-up table.

10. A method according to claim 9, wherein each of the physiological parameters are discretized with respect to 2-10 respective intervals.

11. A method according claim 6, further comprising an input for receiving the at least two physiological parameters.

12. A method according to claim 6, wherein the at least two physiological parameters consist of 2-10 parameters.

13. A method according to claim 12, where the at least two physiological parameters are selected from the set of parameters consisting of pulse, heart rate variability, skin temperature, skin impedance, respiration frequency, eye movements, muscle tonus, $CO_2$ content of the blood, a blood glucose measurement.

14. A method according to claim 13, wherein one of the at least two physiological parameters is a non-invasive blood glucose measurement.

15. A method according to claim 6, wherein the at least two physiological parameters further include the rate of change of at least one of the physiological parameters.

16. A method according to claim 6, wherein the processor is further adapted to compare the identified entry of the look-up table with a predetermined threshold and where the result signal is indicative of the result of said comparison.

17. A method according to claim 6, wherein the output device comprises a structure for generating an audible alarm.

18. A method according to claim 6, wherein the weighting parameter $\lambda$ is provided as:

$$\tau = 1 + (\tau - T_s)/30$$

wherein the predetermined period of time is 30 minutes and the weighting parameter $\lambda$ is linearly increased from $\lambda=0$ at time $T_s-30$, to $\lambda=1$ at time $T_s$, wherein the most recent physiological parameters are weighted more than the older physiological parameters.

19. A method according to claim 6, wherein the probabilities are adjusted by the correction term $\gamma$ modified by a learning rate a wherein the probability is adjusted according to the equation:

$$\Delta P_\tau = P_{i(\tau)} + \alpha(r + \gamma P_{i(\tau)} - P_{i(\tau-1)})$$

wherein the correction term $\gamma$ determines the relative weight of the probabilities at time $\tau$ and at time $\tau-1$ and has a value between 0.97 and 0.98, and the learning rate a determines the overall strength of the correction and has a value between 0.4 and 0.6.

* * * * *

UNITED STATES PATENT AND TRADEMARK OFFICE
CERTIFICATE OF CORRECTION

PATENT NO. : 10,524,669 B2
APPLICATION NO. : 14/055508
DATED : January 7, 2020
INVENTOR(S) : Jette Randlov et al.

It is certified that error appears in the above-identified patent and that said Letters Patent is hereby corrected as shown below:

In the Claims

At Column 17, Claim 5, Line 64, Please replace "rate a" with "rate $\alpha$"

At Column 18, Claim 5, Line 4, Please replace "rate a" with "rate $\alpha$"

At Column 20, Claim 19, Line 26, Please replace "rate a" with "rate $\alpha$"

Signed and Sealed this
Twenty-ninth Day of December, 2020

Andrei Iancu
*Director of the United States Patent and Trademark Office*